United States Patent [19]

Harms et al.

[11] Patent Number: 5,675,040
[45] Date of Patent: Oct. 7, 1997

[54] PROCESS FOR THE PREPARATION OF SULPHONES

[75] Inventors: Wolfgang Harms; Udo-Winfried Hendricks; Karl-Josef Herd, all of Odenthal; Klaus Kunde, Neunkirchen, all of Germany

[73] Assignee: Bayer Aktiengesellschaft, Leverkusen, Germany

[21] Appl. No.: 718,168

[22] Filed: Sep. 19, 1996

Related U.S. Application Data

[62] Division of Ser. No. 456,224, May 31, 1995.

[51] Int. Cl.$^6$ .................... C07C 317/04; C07C 69/14; C07C 69/78
[52] U.S. Cl. ..................... 568/32; 560/103; 560/112; 560/262; 560/264
[58] Field of Search ............... 568/32; 560/103, 560/112, 262, 264

[56] References Cited

U.S. PATENT DOCUMENTS

| | | |
|---|---|---|
| 3,006,963 | 10/1961 | Buc et al. . |
| 3,094,455 | 6/1963 | Allen et al. . |
| 3,509,218 | 4/1970 | Allen et al. . |
| 5,132,461 | 7/1992 | Clausen et al. . |
| 5,405,947 | 4/1995 | Hoppe et al. . |
| 5,439,781 | 8/1995 | MacDowell et al. . |

FOREIGN PATENT DOCUMENTS

| | | |
|---|---|---|
| 0568876 | 11/1993 | European Pat. Off. . |
| 0627667 | 12/1994 | European Pat. Off. . |
| 0629667 | 12/1994 | European Pat. Off. . |
| 4331163 | 3/1995 | Germany . |
| 1156172 | 6/1969 | United Kingdom . |

OTHER PUBLICATIONS

Chemical Abstract, vol. 70, abstract No. 11971p, abstract of Justus Liebigs Ann. Chem., (1968).
A. Schöberl, et al., Liebigs Ann. Chem., vol. 716, pp. 37–46, (1968).
P. D'Agostino, et al., Rapid Commun. Mass. Spectrom., vol. 6, pp. 717–718, (1992).
Organic Reactions, vol. 13, pp. 179–189, 1953.
K.C. Tsou, et al., J. Org. Chem., vol. 26, pp. 4987–4990, (1961).
H. Gilman, J. Am. Chem. Soc., vol. 67, pp. 1847–1848, (1945).
H. Su, et al., J. Org. Chem., vol. 26, pp. 4990–4992, (1961).
Derwent Abstract of JP 61-072-670, (Sep. 14, 1984).

*Primary Examiner*—Nicky Chan
*Attorney, Agent, or Firm*—Sprung Horn Kramer & Woods

[57] ABSTRACT

The invention relates to a process for the preparation of compounds of the formula

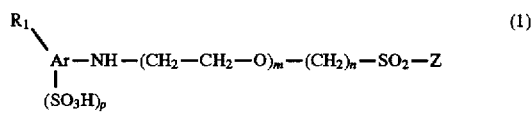

(1)

characterized in that the radical X in sulphones of the formula $$X-(CH_2-CH_2-O)_m-(CH_2)_n-SO_2-CH_2-CH_2OH \quad (2)$$

is replaced by

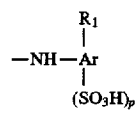

or a compound of the formula

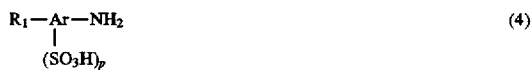

(4)

is added to the sulphone of the formula $$CH_2=CH-SO_2-CH_2-CH_2-OH \quad (3)$$

the substituents having the meanings given in the description.

1 Claim, No Drawings

PROCESS FOR THE PREPARATION OF SULPHONES

This application is a divisional of application Ser. No. 08/456,224, filed on May 31, 1995, now pending.

The present invention relates to a process for the preparation of compounds of the formula

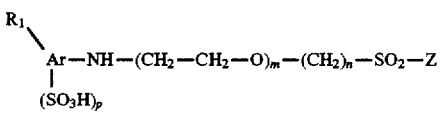
(1)

wherein

Ar=a phenyl or naphthyl radical, $R_1$=H, $C_1$-$C_4$-alkyl, Cl, Br, $C_1$-$C_4$-alkoxy or COOH, acylamino, in particular acetamino or $SO_2$-alkylene-OH, m=0 or 1, n=2, 3 or 4, p=0-2, $Z = -CH=CH_2, -CH_2-CH_2-OSO_3H,$
$-CH_2-CH_2-S_2O_3H, -CH_2-CH_2-OCOCH_3,$
$CH_2-CH_2-OPO_3H_2$ or $-CH_2-CH_2-OH,$ characterised in that the radical X in sulphones of the formula $$X-(CH_2-CH_2-O)_m-(CH_2)_n-SO_2-CH_2-CH_2OH \quad (2)$$

in which

X=Cl, Br, OCO—$(CH_2)_{0-3}$—$CH_3$ or O—CO—$C_6H_5$, is replaced by

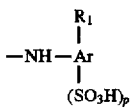

or a compound of the formula, in particular an aniline of the formula

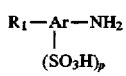
(4)

wherein $R_1$ and p have the abovementioned meanings, is added to the sulphone of the formula $$CH_2=CH-SO_2-CH_2-CH_2-OH \quad (3)$$

The resulting compound of the formula

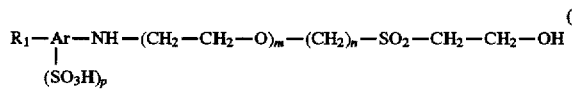
(5)

in which

Z=—$C_2H_4$—OH, can be converted in the customary manner by functionalisation of the OH group into compounds in which Z has one of the other abovementioned meanings.

In one preferred variant, if p=0, $SO_3H$ groups are optionally additionally introduced into the aromatic radical.

The present invention also relates to sulphones of the formula $$X-(CH_2-CH_2-O)_q-(CH_2)_r-SO_2-CH_2-CH_2OH \quad (6)$$

wherein

X=Cl, Br, OCO—$(CH_2)_{0-3}$—$CH_3$ or O—CO—$C_6H_5$, q=0 or 1 and r=2, 3 or 4, if q=1, or r=3 or 4, if q=0, and the process for the preparation of sulphones of the formula (6), characterised in that thioethers of the formula $$X-(CH_2-CH_2-O)_q-(CH_2)_r-S-CH_2-CH_2-OH \quad (7)$$

wherein q and r have the abovementioned meaning, are oxidised in an aqueous or aqueous-organic solution, preferably with hydrogen peroxide, using tungsten or vanadium compounds as catalysts.

Thioethers of the formula (7) are known and described in several literature references:

Tsou et al. Journal of Organic Chemistry 26 (1961) 4987–89,

Su et al. Journal of Organic Chemistry 26 (1961) 4990,

Gilman, Tolman Journal Americ. Soc. 67 (1945) 1848,

D'Agostino, Porter Rapid Commun. Mass. Spectrom. 6 (1992) 717.

They can for example be prepared by one-sided reactions of dihalogenated compounds of the formula $$X-(CH_2-CH_2-O)_m-(CH_2)_n-Y \quad (8)$$

wherein

X and Y=Cl or Br and m and n have the abovementioned meanings, with mercaptoethanol or by the appropriately radical-catalysed addition (see for example Organic Reactions Vol. 13, pages 179 and 189) of mercaptoethanol to vinyl compounds such as for example vinyl acetate.

The literature also describes the sulphones of the formula (9), U.S. Pat. No. 3,509,218, and of the formula (10), ibidem, and Schöberl, Biedermann, Liebigs Ann. Chemie 716 (1969) 37–46

$$Cl-CH_2-CH_2-SO_2-CH_2-CH_2OH \quad (9)$$

$$CH_2=CH-SO_2-CH_2-CH_2OH \quad (10).$$

The replacement of the radical X in the sulphones of the formula (2) by a radical, in particular an aniline radical

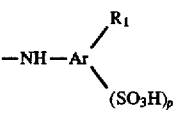

can be carried out in an aqueous, aqueous-organic or purely organic medium, either under controlled pH conditions or in the presence of basic media, such as for example alkali metal carbonate or alkali metal hydrogen carbonate, alkali metal phosphates, alkali metal hydroxide, calcium oxide or magnesium oxide.

Controlled pH conditions are pH values between 5 and 12. The optimum pH value depends on the structure of the sulphone (2).

Solvents which can be used for the substitution reaction are $C_1$-$C_5$-alcohols, acetone, methyl ethyl ketone, N-methylpyrrolidone, dimethylformamide, dimethylsulphoxide or tetramethylenesulphone.

In principle it is possible to carry out the oxidation of the thioether to form the sulphones (2) and the replacement of the substituent X in the sulphones to form the compounds of the formula (1) either in an aqueous or an aqueous-organic medium and directly, without any intermediate isolation of the sulphone (2) being necessary.

The compounds of the formula (1) prepared by the abovementioned process are valuable intermediates for the synthesis of reactive dyestuffs which are used in particular for dyeing natural and regenerated cellulose fibres.

The compounds of the formula (1) can be used for the synthesis of the above types of dyestuffs of the formula (4a)

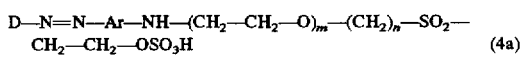
$$\text{CH}_2\text{—CH}_2\text{—OSO}_3\text{H} \quad (4a)$$

wherein

D denotes the radical of a diazo component and m and n have the abovementioned meaning, using for example diazonium salts as coupling components.

The compounds of the formula (1) are however preferably used for the synthesis of high fixation bifunctional reactive dyestuffs of the formula

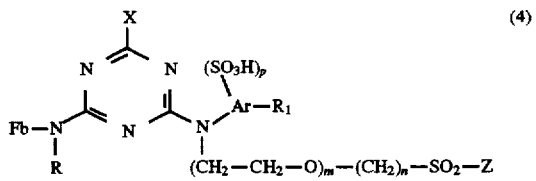

wherein

Z, $R_1$, p, m and n have the meaning given under compound (1) and

X=F, Cl, or Br,

R=H or $C_1$–$C_4$-alkyl and

Fb=the radical of a dyestuff of the mono- or polyazo, metal complex azo, anthraquinone, phthalocyanine, formazan, azomethine, dioxazine, phenazine, stilbene, triphenylmethane, xanthene, thioxanthone, nitroaryl, naphthoquinone, pyrenequinone or perylene tetracarbimide series, by condensation with trihalotriazines and dye bases containing amino groups.

EXAMPLE 1

A. 129 g of vinyl acetate and 140.4 g of 2-mercaptoethanol are mixed together. 1.5 g of azo-bis-(isobutyronitrile) is added with stirring and the stirring of the mixture is continued, during which the temperature increases to 30° C. within about 30 minutes. The mixture is stirred overnight at room temperature and is then heated for 8 hours to 50° C., until a sample dissolved in DMSO no longer produces the $^1$H-NMR signals at 7.2 ppm which are characteristic of vinyl acetate (splitting of the individual CH vinyl proton into a quartet) or those of the $CH_2$ vinyl protons (each split into doublets) at 4.6 ppm and 4.85 ppm.

A colourless oil is obtained, the main component of which corresponds to the formula

$^1$H-NMR in $D_6$-DMSO (TMS as the internal standard)

δ = 2.00 ppm(s, 3H)
= 2.60 ppm(t, 2H)
= 2.76 ppm(t, 2H)
= 3.55 ppm(m, 2H)
= 4.13 ppm(t, 2H)
= 4.79(t, 1H)

B. 81.3 g of the thioether of Example 1A in the form of an oil are stirred with 225 ml of water and 5.25 g of Na acetate; the pH value is adjusted to 5.2 using about 1.5 ml of glacial acetic acid and a catalyst solution is added which has been obtained from 1.5 g of tungstic acid by neutralising with sodium hydroxide solution in 30 ml of water and adjusting the pH value to 5.2 using 2.4 ml of glacial acetic acid.

90.0 g of 35% hydrogen peroxide are added dropwise at 55° C., the pH value being kept at 5.0–5.2 using 2N sodium hydroxide solution. Additional 35% hydrogen peroxide is subsequently added in such an amount that a slight excess is maintained. A further 20–30 g are usually required for this purpose. As soon as the total quantity of sulphoxide has been oxidised to form the sulphone after 4 hours at 55°–60° C., as can be determined by examining a sample by thin-layer chromatography, the mixture is cooled to 35° C. A colourless solution is obtained.

If the resulting solution is concentrated in vacuo at 35°–40° C., the substance

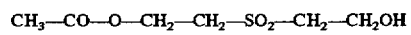

is obtained in the form of a colourless oil which has the following masses according to its mass spectrum obtained by chemical ionisation:

$M_1+H^+=197$
$M_2+H^+=155$ (cleavage of $CH_3$—CO)
$M_3+H^+=137$ (cleavage of $H_2O$)

$^1$H-NMR in $D_6$-DMSO (TMS as the internal standard)

δ = 2,02 ppm(s, 3H)
= 2.66 ppm(t, 2H)
= 3.51 ppm(t, 2H)
= 3.65 ppm(t, 2H)
= 4.38 ppm(t, 2H)
= 4.6 ppm(broad)

C. 84 g of aniline are added to the colourless solution of 2-acetoxyethyl-2'-hydroxyethylsulphone (0.45 mol) obtained in Example 1B at 50° C. The pH value is adjusted to 6.5 with 2N sodium hydroxide solution and the mixture is stirred for several hours at 55° C. and a pH of 6.5 until the chromatographic examination shows the disappearance of acetoxysulphone. Excess aniline is then stripped off in vacuo, at 50°–60° C., together with the water distilled over, until it disappears, and the product isolated is a brownish oil which gradually solidifies to form a wax-like substance.

Yield: 186 g with a content of 34% (HPLC) of the compound of the formula

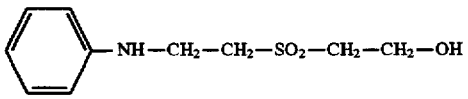

(Yield of 61% of theory based on the vinyl acetate used in Example 1A).

The isolated and rigorously dried product has the following physical properties:

Melting point after rigorous drying: <50C. Mass spectrum obtained by chemical ionisation: $M_1+H^{\oplus}=230$ $^1$H-NMR in $D_6$-DMSO (TMS as the internal standard)

δ = 3.27–3.38(m, 4H)
  = 3.48–3.53(m, 2H)
  = 3.74–3.82(m, 2H)
  = 5.23(t, 1H)
  = 5.77(t, 1H)
  = 6.55–6.60(m, 3H)
  = 7.05–7.12(m, 2H)

As a secondary component the crude product contains 2–3% of bis-(2-hydroxyethyl)-sulphone, in addition to 34 % of molecular weight 229 of the above formula.

EXAMPLE 2

44 g of aniline are added to the colourless solution of 2-acetoxyethyl-2'-hydroxyethylsulphone (0.45 mol) obtained in Example 1B, the mixture is adjusted to a pH of 7.0 and then stirred for 4 hours at 50° C. and later at 60° C. until the acetoxysulphone disappears. After concentrating the mixture in vacuo the product described in Example 1C is obtained with a similar content.

EXAMPLE 3

44 g of aniline are added to the colourless solution of 2-acetoxyethyl-2'-hydroxyethylsulphone (0.45 mol) obtained in Example 1B and the mixture is maintained at a pH of 6.5 by adding the necessary quantity of 2N sodium hydroxide solution for 12 hours at 50°–55° C., until the examination by thin-layer chromatography or HPLC reveals virtually no remaining content of acetoxysulphone. After concentrating the mixture in vacuo the N-(2-(2'-hydroxyethylsulphonyl)-ethyl)-aniline described in Example 1C is obtained in a similar form and quality.

EXAMPLE 4

The test of Example 3 is repeated using 66 g of aniline, but otherwise using the same procedure and the mixture is worked up by stripping off the excess aniline, together with water vapour, by vacuum distillation, after which a product corresponding to that of Example 1C is obtained.

EXAMPLE 5

The test of Example 4 is repeated, except that the pH value is maintained at 5.5 for the purpose of replacing the acetoxy group by the aniline radical.

EXAMPLE 6

The test of Example 4 is repeated, except that the pH value is kept at 7.5–8.0 for the purpose of replacing the acetoxy group by the aniline radical.

Additional products of the general formula

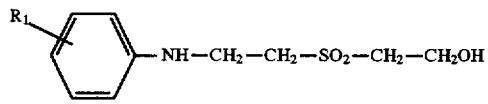

are obtained when the following substituted anilines are used in Examples 2 to 7 instead of the aniline:

| Example no. | substituted aniline |
| --- | --- |
| 7 | o-toluidine |
| 8 | p-toluidine |
| 9 | m-toluidine |
| 10 | p-anisidine |
| 11 | m-anisidine |
| 12 | o-anisidine |
| 13 | p-chloroaniline |
| 14 | 4-acetaminoaniline |
| 15 | 3-acetaminoaniline |
| 16 | 3-aminobenzenesulphonic acid |
| 17 | 4-aminobenzenesulphonic acid |
| 18 | 2-aminonaphthalene-5-sulphonic acid |
| 19 | 3-aminophenyl-2'-hydroxyethylsulphone |
| 20 | 3-aminobenzoic acid |
| 21 | 4-aminobenzoic acid |
| 22 | 2-aminobenzoic acid |

EXAMPLE 23

80.0 g of the sulphone of the formula

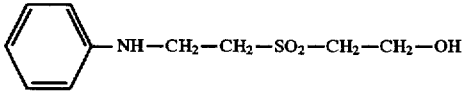

obtained according to Examples 2–5 are introduced into 40 ml of 96% sulphuric acid at 20°–30° C. and the mixture is stirred for 3 hours. 50 ml of 20% oleum are added dropwise with cooling at 10°–15° C. and the mixture is stirred for a further 2–3 hours, until visually no more starting product can be detected in the thin-layer chromatogram. The resulting solution is poured onto 900 g of ice water. 210–220 g of calcium carbonate are then introduced into the diluted sulphuric acid suspension until a pH value of 5.0 is obtained.

After filtering off the calcium sulphate, washing the precipitate and concentrating the combined filtrates to the required volume, a solution of the compound

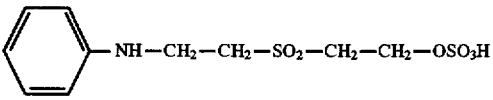

is obtained in a yield of 94% (titration with sodium nitrite).

EXAMPLE 24

If the procedure of Example 23 is repeated using identical quantities of N-(2-(2-hydroxyethylsulphonyl)-ethyl)-aniline, 96% sulphuric acid and 20% oleum, and the resulting solution is finally introduced with cooling into 500 g of ice, and the mixture is subsequently stirred for 1 hour at 0°–5° C., a precipitate of the product of the formula

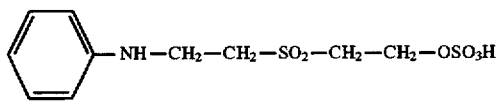

is obtained in a yield of 55–65% in the form of a light brown precipitate which can be freed from sulphuric acid residues by stirring it into isopropanol, filtering by suction and washing with isopropanol.

$^1$H-NMR in $D_6$-DMSO (TMS as the internal standard)

δ=3.43 ppm (2H, t)
δ=3.50 ppm (2H,t)
δ=3.60 ppm (2H,t)
δ=4.11 ppm (2H, t)
δ=7.00 ppm (3H, d, d)
δ=7.30 ppm (2H, t)
δ=8.98 ppm (2H, s)

EXAMPLE 25

A. 81.3 g of 2-acetoxyethyl-2'-hydroxyethyl sulphide from Example 1A are dissolved in 150 ml of N-methyl-2-p-pyrrolidine. A solution of 2.0 g of sodium tungstate ($Na_2WO_4.2H_2O$) in 10 ml of water, which has been adjusted to a pH of 5.5 with glacial acetic acid, is added and 90.0 g of 35% hydrogen peroxide are introduced at 50° C. with cooling.

The temperature is kept at 50° C. and the pH value is kept at 5.0–5.2 with 2N sodium hydroxide solution.

These conditions are maintained and, if necessary, an additional quantity of hydrogen peroxide required to obtain complete oxidation to form 2-acetyloxyethyl-2'-hydroxyethyl sulphone is added after 2 hours.

B. When the oxidation is complete 44 g of aniline are added. The pH value is then maintained at 6.5 and the mixture is stirred for several hours at 100° C. until the acetoxyethyl compound has disappeared. A solution of the product of the formula

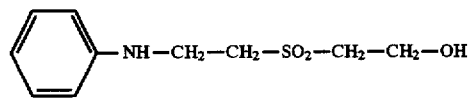

is obtained. The water is distilled off from the resulting solution in vacuo (1 mm).

If 70 g of chlorosulphonic acid are added to the N-methylpyrrolidone solution of N-(2-(2'-hydroxyethylsulphonyl)-ethyl)-aniline obtained according to Example 25B, the disappearance Of the starting product is confirmed, and the resulting solution is poured onto 300 g of ice with cooling and neutralised with solid lithium carbonate or a 15% soda solution at 0°–5° C., a solution of the compound

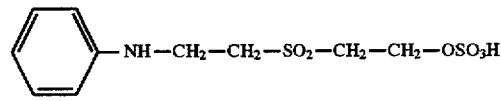

is obtained which can be processed further directly.

EXAMPLE 26

45.8 g of N-(2-(2-hydroxyethylsulphonyl)-ethyl)-aniline are introduced at 20°–25° C. into a mixture of 120 ml of 20% and 35 ml of 65% oleum. The solution is heated to 40° C. If the examination of the product reveals no remaining content either of the starting product or of the sulphato compound described in Examples 23, 24 and 25, the reaction solution is poured onto 900 g of ice and 300 ml of water.

The resulting brown solution is neutralised at 0°–10° C. with about 325 g of calcium carbonate until a pH value of 5.5 is obtained. The precipitated calcium sulphate is filtered off, washed free of the product with water and, after concentration, a brown solution of the compound of the formula

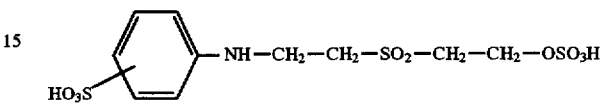

(isomeric sulphonic acids m:p=70:30) is obtained in a yield of 94% (titration with sodium nitrite HCl).

If the solution is evaporated to dryness, a brown, viscous substance remains which can be converted into a sand-coloured powder by trituration with isopropanol. The product is dried in an air-circulation cabinet.

$^1$H-NMR in $D_6$-DMSO (TMS as the internal standard)

|  | signal integration |
|---|---|
| δ = 3.35 ppm (m, 2H) | } 8H |
| δ = 3.42–3.58 ppm (m, 4H) | |
| δ = 4.10–4.16 ppm (m, 2H) | |
| δ = 6.58 ppm (d, 2H, p-isomer) | |
| δ = 7.40 ppm (d, 2H, p-isomer) | } 4H |
| δ = 6.63–6.69 ppm (d, d, 1H, m-isomer) | |
| δ = 6.90 ppm (s, 1H, m-isomer) | |
| δ = 6.95 ppm (d, 1H, m-isomer) | |
| δ = 7.13–7.20 ppm (t, 1H, m-isomer) | |

EXAMPLE 27

The solution of 2-acetoxyethyl-2'-hydroxyethyl sulphone (0.45 mol) obtained in Example 1B is maintained at a pH of 10 with 2N sodium hydroxide solution at room temperature for several hours, until the consumption of sodium hydroxide solution comes to a standstill and the formation of 2-hydroxyethyl-vinyl sulphone is complete. 44 g of aniline are added to the solution, which is heated to 50° C. for 6 hours until the addition of aniline is complete. After subsequent concentration in vacuo an oil remains, the main component of which consists of N-(2-(2'-hydroxyethylsulphonyl)-ethyl)-aniline.

EXAMPLE 28

54.4 g of 2-hydroxyethyl-vinylsulphone, produced as described by A. Schöberl and M. Biedermann in Liebigs Ann. Chemie 716, 37–46 (1968) are stirred into 400 ml of water. After adding 45 g of aniline the pH value is adjusted to 8–9 and the mixture is heated to 50°–55° C. for several hours until the vinyl compound has be completely converted. After removing the excess aniline with water vapour in vacuo a slowly solidifying oil of N-(2-(2'-hydroxyethylsulphonyl)ethylaniline is obtained as a residue with the physical data mentioned in Example 2.

EXAMPLE 29

60.0 g of 3-chloropropyl-2'-hydroxyethyl sulphide, produced by reacting 1,3-bromochloropropane with 2-mercaptoethanol (cf. Journal Americ. Soc. 67 (1945) 1848) are stirred into 180 ml of water and 4.5 g of sodium acetate. A solution of 1.2 g of tungstic acid in 30 ml of water and 1.8 ml of a 50% sodium hydroxide solution are added and the pH value is then adjusted to 5.2 with 3.0 ml of glacial acetic add. 38.7 g of 35% hydrogen peroxide are then added dropwise over a period of 40 minutes at 25°–30° C., during which the emulsion initially present is converted into a clear solution. An additional 38.7 g of 35% hydrogen peroxide are added dropwise, during which the temperature is increased to 45°–50° C. and the pH value is kept at 5.2 by adding 6–7 ml of 2N soda solution dropwise. The mixture is kept at 50° C. for a further 1–1½ hours if the test for $H_2O_2$ is positive until no more sulphoxide is detected by chromatographic examination.

The resulting solution can be processed further in its existing form for the purpose of chlorine substitution. If the isolation of the product is required, the reaction solution is evaporated in vacuo in a rotary evaporator, the residue is taken up in 300 ml of methylene chloride, and the salts are filtered off by suction, subsequently washed with methylene chloride and the combined filtrates are evaporated. The compound of the formula

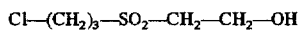

Cl—(CH$_2$)$_3$—SO$_2$—CH$_2$—CH$_2$—OH is obtained in the form of a light yellow oil in a yield of 70.2 g=97% of theory.

$^1$H-NMR in D$_6$-DMSO (TMS as the internal standard)

δ=2.12–2.24 (m, 2H)

δ=3.23–3.28 (m, 4H)

δ=3.73–3.381 (m, 4H)

δ=about 5.2 (broad, 1 H)

EXAMPLE 30

37.9 g of aniline and 34.4 g of sodium hydrogen carbonate are added to the solution of 70.2 g of 3-chloropropyl-2'-hydroxyethyl sulphone obtained in Example 29 or a solution of 70.2 g of the isolated sulphone in 280 ml of water. The emulsion is heated to 100° C. for 12 hours, until the chromatographic examination confirms the complete substitution of the chlorine atom by the aniline radical. Excess aniline is stripped off by water vapour in vacuo and after sedimentation a brown oil is obtained, which is isolated. After extracting the aqueous phase with 200 ml of methylene chloride the isolated oil and the methylene chloride phase are combined, washed with 150 ml of water and dried over sodium sulphate. After concentrating the methylene chloride solution, finally in vacuo, 68.0 g=74% of theory of a light brown oil of the formula

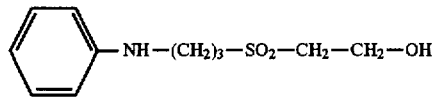

are obtained as the residue: mass spectrum molecular weight M$^+$=243

$^1$H-NMR in D$_6$-DMSO (TMS as the internal standard)

δ=1.92–2.03 (m, 2H)

δ=3.09–3.24 (m, 6H)

δ=3.79–3.85 (m, 2H)

δ=5.08–5.12 (t, 1H)

δ=5.58–5.62 (t, 1H)

δ=6.48–6.58 (m, 3H)

δ=7.04–7.10 (t, 2H)

EXAMPLE 31

64.8 g of N-3-(2-hydroxyethylsulphonyl)-propylaniline from Example 30 are added dropwise into a mixture of 54 ml of 96% sulphuric acid and 54 ml of 20% oleum over a period of one hour. The temperature of the reaction mixture is maintained at 20°–25° C. by cooling. If, after subsequent stirring for 2 to 3 hours, the chromatographic examination reveals virtually no remaining starting product the mixture is poured onto 600 g of ice. The solution is neutralised over approximately 1½ hours by adding about 309 g of calcium carbonate until a pH of 5.0 is obtained, the precipitated calcium sulphate is filtered off with suction, washed with about 2 l of water and the filtrate and washing liquid are concentrated in vacuo at 12–15 mm Hg to a residual volume of about 600 ml.

The resulting solution of the compound

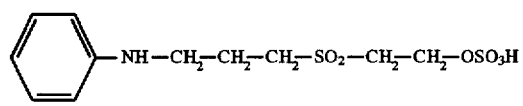

the content of which is determined by titration with a sodium nitrite solution, can be used directly for the production of reactive dyestuffs, for example by condensation with cyanuric fluoride or cyanuric chloride, followed by the reaction of the condensation product with an amino-group-containing dye base.

If the sulphuric acid half-ester is required to be isolated in the form of a salt, the solution obtained after the precipitation of the calcium sulphate is concentrated after repeated, intermediate filtration, and the concentrated residue is stirred with isopropanol, filtered off by suction and dried.

EXAMPLES 32–45

Further products of the general formula

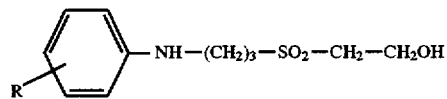

are obtained if the following substituted anilines are used in Example 30 instead of the aniline:

| Example no. | substituted aniline |
| --- | --- |
| 32 | p-toluidine |
| 33 | m-toluidine |
| 34 | o-toluidine |
| 35 | p-anisidine |
| 36 | m-anisidine |

-continued

| Example no. | substituted aniline |
|---|---|
| 37 | o-anisidine |
| 38 | 3-aminobenzenesulphonic acid |
| 39 | 3-aminophenyl-2'-hydroxyethylsulphone |
| 40 | 4-aminophenyl-2'-hydroxyethylsulphone |
| 41 | 4-acetaminoaniline |
| 42 | 3-acetaminoaniline |
| 43 | 3-aminobenzoic acid |
| 44 | 4-aminobenzoic acid |
| 45 | 3-nitroaniline |

EXAMPLE 46

33.7 g of 4-chloro-1-butyl-2'-hydroxyethyl sulphide, produced by reacting 1,4-dichlorobutane with 2-mercaptoethanol (as described by Tsou et al., J. Org. Chem. 26 (1961), 4989), are stirred into 150 ml of water and 2.3 g of sodium acetate. After adding 0.6 g of tungstic acid in 15 ml of water and 0.9 ml of 50% sodium hydroxide solution, the thioether is oxidised in the manner described in Example 29 with 41 g of 35% hydrogen peroxide at a final temperature of 45°–50° C. and a solution of the sulphone of the formula

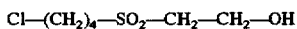
Cl—(CH$_2$)$_4$—SO$_2$—CH$_2$—CH$_2$—OH is obtained, which is reacted, as described in Example 30, after adding 20.0 g of aniline and 17 g of sodium hydrogen carbonate at 100° C. to form the compound of the formula

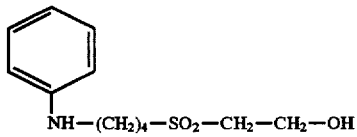
NH—(CH$_2$)$_4$—SO$_2$—CH$_2$—CH$_2$—OH which can be isolated in the form of a light brown oil in the manner described in Example 30.

EXAMPLE 47

36.9 g of 2-(2-chloroethoxy)-ethyl-2'-hydroxyethyl sulphide, $^1$H-NMR in D$_6$-DMSO (TMS as the internal standard)

δ=2.56–2.62 (t, 2H)

δ=2.68–2.74 (t, 2H)

δ=3.48–3.61 (t, t 4H)

δ=3.66–3.73 (m, 4H)

δ=4.74 (t, 1 H), produced by reacting 2-(bis-chloroethyl) ether with mercaptoethanol, are stirred into 150 ml of water and 2.3 g of sodium acetate and, after adding a solution of 0.6 g of tungstic acid in 15 ml of water and 0.9 ml of 50% sodium hydroxide solution, the mixture is oxidised with 42 g of 35% hydrogen peroxide at temperatures controlled stepwise, initially at 30° C. with cooling and in the second stage at 55°–60° C. A solution is obtained from which, after concentration in vacuo, the sulphone of the formula

Cl—CH$_2$—CH$_2$—O—CH$_2$—CH$_2$—SO$_2$—CH$_2$—CH$_2$—OH is precipitated in the form of a colourless oil: mass spectrum obtained by chemical ionisation: M+H$^+$=217/219

$^1$H-NMR in D$_6$-DMSO (TMS as the internal standard)

δ=3.25–3.30 (t, 2H)

δ=3.38–3.43 (t, 2H)

δ=3.69–3.74 (m, 4H)

δ=3.78–3.86 (m, 4H)

δ=4.64 (broad, 1H)

If the aqueous solution of the abovementioned sulphone is not concentrated and 20.0 g of aniline and 17 g of sodium hydrogen carbonate are added, the mixture is heated to 100° C. and otherwise the same procedure is used as described in Example 30, the compound of the formula

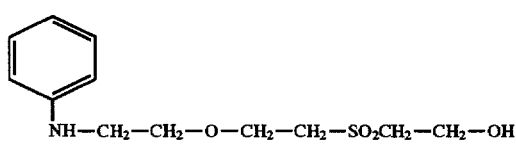
NH—CH$_2$—CH$_2$—O—CH$_2$—CH$_2$—SO$_2$CH$_2$—CH$_2$—OH is obtained, which can be isolated in the form of a brownish oil in the manner described in Example 30:

mass spectrum obtained by chemical ionisation: M$_1$+H$^+$ =274 M$_1$+H$^+$–H$_2$O=256

EXAMPLE 48

A) 0.15 mol of the compound of the formula

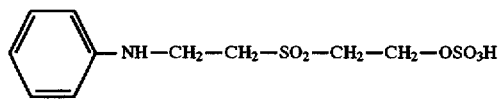
NH—CH$_2$—CH$_2$—SO$_2$—CH$_2$—CH$_2$—OSO$_3$H are mixed with 100 parts of water and 100 parts of ice and the mixture is neutralised with Na$_2$CO$_3$. 0.17 mol of 2,4,6-trifluoro-1,3,5-triazine are added dropwise to this solution at 0° C. over a period of 10 minutes and the pH is maintained at 4.5 to 5. 250 parts of a condensation solution of the following compound

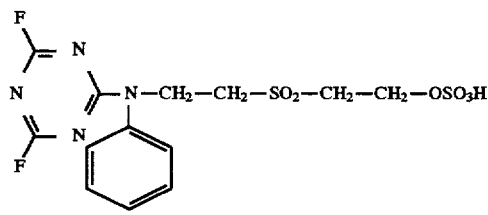

are obtained.

B) 0.1 mol of the copper complex of N-(2-carboxy-5-sulphophenyl)-N'-(2'-hydroxy-3'-amino-5'-sulphophenyl)-ms-phenyl-formazan-di-sodium salt are dissolved in 600 ml of water. After cooling to 0° to 5° C. the solution of the component prepared in Example 48A is introduced and the pH value is maintained at 7.0 to 8.0 by adding a soda solution. After 2 hours the temperature is allowed to rise gradually to 20° C. and the dyestuff is salted out after the condensation is complete, and the product is filtered off and, after buffering at pH 6, dried in vacuo at 45° C.

The dyestuff of the formula

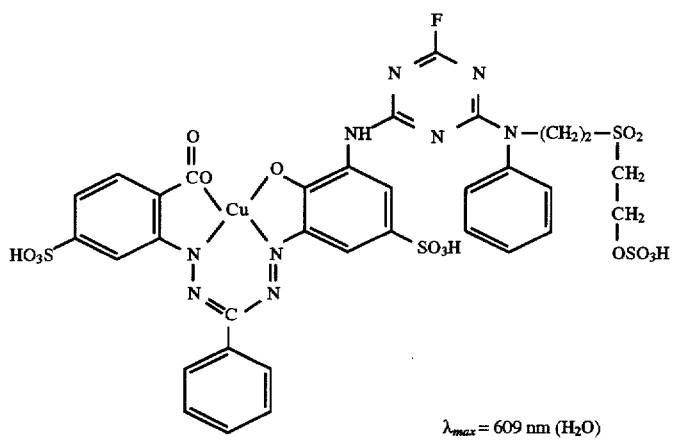

$\lambda_{max}$ = 609 nm (H$_2$O)

dyes cotton in a long bath in blue shades with very high fixation yields.

EXAMPLE 49

A) 11.0 g of cyanuric chloride are suspended in 100 ml of ice water. 0.5 ml of an emulsifier is added. A solution of 56 mmol of the component of Example 31 of the formula

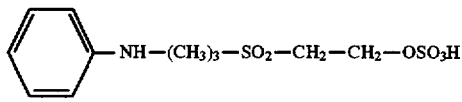

in 300 ml of water is added dropwise at 0°–5° C., during which addition the pH value is maintained at 4.2–4.5 with 2N soda solution. After removal of small quantities of cyanuric chloride residues the solution of the resulting condensation product is added to a neutral solution of 0.45 mol of the monoazo compound of the formula

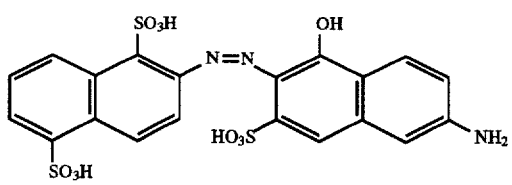

The mixture is maintained at a pH of 6.5 with 2N soda solution. The temperature is initially kept at 30° C. for 2 hours, is then raised to 40° C. for several hours and finally to 50° C., until the reaction solution hardly contains any remaining monoazo starting product. The dyestuff is salted out of the solution using 15% by weight of sodium chloride, filtered off by suction, washed with a sodium chloride solution and, after buffering at a pH of 6, dried in vacuo at 45° C. An orange-coloured powder is obtained.

The dyestuff corresponds to the formula

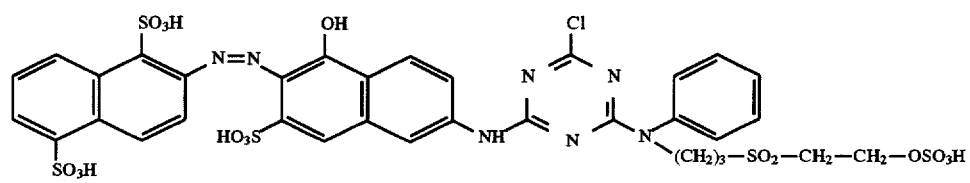

$\lambda_{max}$ = 486 nm in water.

$\lambda_{max}$ = 486 nm in water.

It dyes cotton in a long bath with a high fixation yield.

We claim:

1. Sulphones of the formula $$X-(CH_2-CH_2-O)_q-(CH_2)_r-SO_2-CH_2-CH_2-OH \quad (2)$$

wherein

X=Cl, Br, OCO—(CH$_2$)$_{0-3}$—CH$_3$ or O—CO—C$_6$H$_5$, q=0 or 1, r=2, 3 or 4, if q=1, and r=3 or 4, if q=0.

* * * * *